US007290973B2

(12) United States Patent
Sato et al.

(10) Patent No.: US 7,290,973 B2
(45) Date of Patent: *Nov. 6, 2007

(54) AUTOMATIC STORAGE SYSTEM

(75) Inventors: Koji Sato, Hitachinaka (JP); Sadato Igarashi, Hitachinaka (JP)

(73) Assignee: Hitachi Koki Co., Ltd., Tokyo (JP)

( * ) Notice: Subject to any disclaimer, the term of this patent is extended or adjusted under 35 U.S.C. 154(b) by 357 days.

This patent is subject to a terminal disclaimer.

(21) Appl. No.: 10/638,321

(22) Filed: Aug. 12, 2003

(65) Prior Publication Data
US 2004/0037679 A1 Feb. 26, 2004

(30) Foreign Application Priority Data
Aug. 21, 2002 (JP) .............. P2002-241132

(51) Int. Cl.
*B65G 1/06* (2006.01)
(52) U.S. Cl. ...................................... 414/281
(58) Field of Classification Search ............... 414/281, 414/331.05, 279, 280; 422/63; 62/177; 435/287.3
See application file for complete search history.

(56) References Cited

U.S. PATENT DOCUMENTS

| | | | | | |
|---|---|---|---|---|---|
| 3,575,692 | A | * | 4/1971 | Gilford | ........................ 422/65 |
| 3,687,632 | A | * | 8/1972 | Natelson | .................. 73/864.25 |
| 4,678,390 | A | * | 7/1987 | Bonneton et al. | ........... 414/282 |
| 5,362,648 | A | * | 11/1994 | Koreyasu et al. | ............. 436/48 |
| 5,967,339 | A | * | 10/1999 | Utsumi et al. | ........... 211/41.12 |
| 5,998,799 | A | * | 12/1999 | Cremer et al. | .......... 250/504 R |
| 6,068,437 | A | | 5/2000 | Boje et al. | |
| 6,099,096 | A | * | 8/2000 | Lambright | ................ 312/321.5 |
| 6,357,983 | B1 | | 3/2002 | Junca | |
| 6,445,651 | B1 | * | 9/2002 | Felde et al. | .............. 369/30.41 |
| 6,700,734 | B2 | * | 3/2004 | Satoh | .......................... 360/92 |
| 6,890,485 | B1 | * | 5/2005 | Stylli et al. | ................. 422/68.1 |
| 6,919,044 | B1 | * | 7/2005 | Shibata et al. | ................. 422/63 |
| 2001/0030492 | A1 | * | 10/2001 | Branz et al. | ................. 312/236 |

FOREIGN PATENT DOCUMENTS

| | | |
|---|---|---|
| EP | 0 846 636 A1 | 6/1998 |
| JP | 2002-205804 | 7/2002 |
| JP | 2002-234601 | 8/2002 |
| WO | WO 02/37123 A1 | 5/2002 |

OTHER PUBLICATIONS

European Search Report dated Nov. 13, 2003.

* cited by examiner

*Primary Examiner*—Charles A Fox
(74) *Attorney, Agent, or Firm*—McGuireWoods LLP

(57) ABSTRACT

First and second shelf sections are positioned side by side in an outer frame having front left and right doors. The first self section is fixed to a rear wall of the outer frame, and the second shelf section is secured to the front left and right doors. By opening the front left and right doors, access to the first self section is facilitated for storing a plurality of racks therein, the racks holding sample containers. A transfer section is movable along a linear space defined between the first and second shelf sections. The transfer section includes a pair of rack pull-out mechanisms each for pulling out each rack stored in the shelf sections. A repacking mechanism including a picker mechanism is provided on the transfer section for moving a sample container from the rack on the first rack pull-out mechanism to a rack on the other rack pull-out mechanism.

16 Claims, 5 Drawing Sheets

AUTOMATIC STORAGE SYSTEM

BACKGROUND OF THE INVENTION

The present invention relates to an automatic storage system used in the field of medical science, pharmacy, agriculture, clinical medicine, and bio-technology. More particularly, the invention relates to such automatic storage system for storing a plurality of sample containers and picking up a selected sample container(s).

As a result of technological innovation in various fields such as medical science, pharmacy, agriculture, clinical medicine, and bio-technology, various kinds of testing samples must be investigated. To this effect, greater numbers of sample containers accumulating therein various kind of testing samples such as blood, ferment, gene, a chemical compound, a chemical reagent must be stored and picked-up for the investigation.

A conventional automatic storage system is shown in FIGS. 9 and 10. The storage system includes a storage section 110 for storing a plurality of sample containers 2 accommodated in a plurality of racks 3, a transfer section 120 for picking-up a rack 3 from the storage section 110, and a repacking section 126 for picking up one or several sample containers from the rack 3 or accommodating other sample container(s) into the rack 3. The storage system also includes a control section 130 for controlling operation of the storage section 110, the transfer section 120 and the repacking section 126.

In the storage section 110, a plurality of shelves 114 area arrayed side by side, and these shelves 114 are circularly moved as shown by an arrow F in FIG. 9. In each shelf 114, a plurality of racks 3 are vertically arrayed and held in positions. The storage section 110 has an elongated configuration.

The transfer section 120 is positioned at one longitudinal end of the storage section 110. The transfer section 120 includes an arm robot and a belt conveyer movable in both horizontal and vertical direction as shown by arrows G and H for picking up a selected one of the racks 3 from a selected one of the shelf 114 moved and stopped beside the transfer section 120 and for transferring the selected rack 3 to the repacking section 126. The transfer section 120 is also adapted for transferring the rack 3 from the repacking section 126 to the storage section 110.

The repacking section 126 is positioned beside the transfer section 120 at a position opposite to the storage section 110. The repacking section 126 includes a picker mechanism 129 and a stand 122 on which a receptible rack 4 is to be mounted. The picker mechanism 129 is adapted for picking up a selected sample container 2 from the rack 3 and accommodates the selected sample container 2 into the receptible rack 4. The repacking section 126 is also adapted for accommodating a sample container 2 from the receptible rack 4 to the rack 3.

The control section 130 stores therein data indicative of position of each sample container 2 and each rack 3, and transmits command signal to the storage section 110, the transfer section 120 and the repacking section 126. More specifically, when a specific sample container 2 is input through the control section 130, the storage section 110 performs circular movement so that a specific rack 3 accommodating therein the specific sample container 2 can be positioned in confrontation with the transfer section 120 based on the position data of the racks and the sample containers. Then, the transfer section 120 picks up the specific rack 3 from the storage section 110, and transfers the specific rack 3 to the repacking section 126 where the picker mechanism 129 picks-up the specific sample container 2 from the specific rack 3, and accommodates the specific sample container 2 into the receptible rack 4 mounted on the case stand 122. Then the specific rack 3 is returned to the storage section 110 by the transfer section 120. This operation is repeatedly performed so that desired sample containers 2 can be accommodated into the receptible rack 4.

The above described conventional automatic storage system becomes bulky due to linear orientation among the storage section 110, the transfer section 120 and the repacking section 126. Therefore, a large room is required for setting the storage system.

Further, in the conventional system, the numbers of the testing tubes picked up from the racks 3 is dependent on the capacity of the receptible rack 4. The numbers of the sample containers 2 to be picked up can be increased by using a plurality of receptible racks 4. In the latter case, the plurality of receptible racks 4 are stored in the storage section 110. However, the numbers of the receptible racks 4 may be limited due to storage capacity of the storage section 110 where a plurality of racks 3 are also stored.

To overcome this problem, another storage section may be provided for exclusively storing the plurality of receptible rack 4. However, in this case, another robot must be required for automatically supplying the receptible rack(s) from the other storage section to the repacking section 126. As a result, an entire storage system becomes extremely bulky and costly.

Further, due to repeated picking-up and storing operations, sample containers 2 may be scattered over various racks 3. Therefore, the sample containers must be in trim order in the reduced numbers of racks 3. For the proper arrangement of the sample containers, an operator must be manually repack the sample containers among the racks in the storage section 110. However in this case, the position data of the sample containers and racks may be destroyed.

In the conventional automatic repacking operation, the storage section 110 must perform circular movement until the desired rack 3 is brought into confrontation with the transfer section 120, and this circular movement must be performed each time the desired sample container must be picked up by the picker mechanism 129 from each rack 3 while the identical receptible rack 4 remains on the stand 122. Such process is extremely complicated.

Moreover, storage work for storing each one of the sample containers 2 into the storage section 110 can be easily performed in the conventional automatic storage system. However, extremely prolonged period must be required in order to store great numbers of sample containers at once into the storage section 110 in case of the initial setting.

Japanese patent application Publication No.2002-205804 discloses storage shelves positioned side by side, and an automatic pick-up device runs between the storage shelves for picking up a desired rack from the shelf, and for transferring the picked up rack to a transfer box outside of the shelves. Further, an external station is positioned for picking up a container or a test tube accommodated in the rack.

Japanese patent application Publication no. 2002-234601 discloses a pair of shelves each circularly moved in a vertical direction. A rail extends through a space between the pair of shelves, and a transfer unit runs along the rail.

SUMMARY OF THE INVENTION

It is an object of the present invention to overcome the above-described problems and to provide an improved automatic storage system capable of randomly setting numbers of the sample containers to be picked up, and automatically properly arranging the sample containers in the storage section, and allowing great numbers of sample containers to be stored rapidly particularly at an initial setting up.

These and other objects of the present invention will be attained by an automatic storage system for storing sample containers held in racks including an outer frame, first and second shelf sections, a transfer section, and a control section. The outer frame has a rear wall, a front side formed with a front opening, and a front door. The front door is pivotally movably secured to the front side for opening and closing the front opening. The first shelf section is positioned in the outer frame and is secured to the rear wall for storing a plurality of racks in which a plurality of sample containers are installable. The second shelf section is positioned in the outer frame and is secured to the front door for storing a plurality of racks in which a plurality of sample containers are installable. The first shelf section and the second shelf section are positioned side by side with a space therebetween. The transfer section is movable in the space and includes a rack pull-out mechanism for pulling out the rack from either one of the first and second shelf sections, maintaining the pulled-out rack on the rack pull-out mechanism and returning the pulled-out rack to one of the first and second shelf sections. The control section is connected to the transfer section for managing operation thereof and managing position data of the racks and sample containers.

DETAILED DESCRIPTION OF THE PREFERRED EMBODIMENTS

Figure 1:
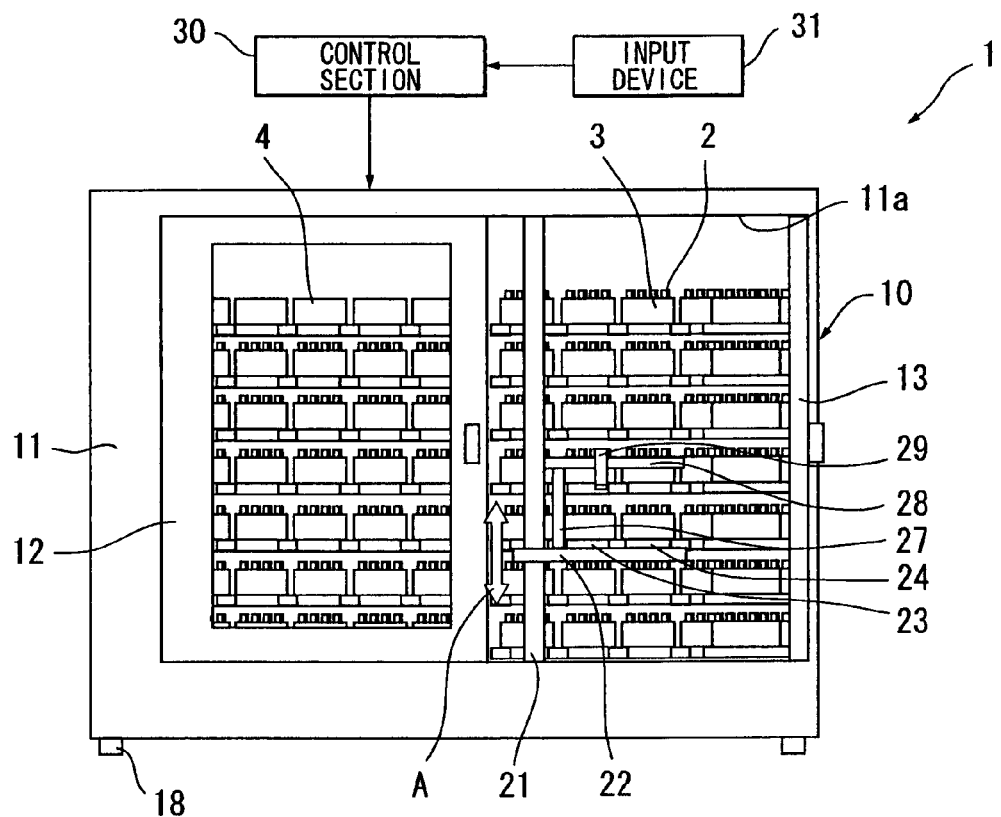
FIG. 1 is a front view showing an automatic storage system according to one embodiment of the present invention.

An automatic storage system according to one embodiment of the present invention will be described with reference to FIGS. 1 through 8. A plurality of box shaped racks 3 and a plurality of box shaped receptible racks 4 are used. Each rack 3 and receptible rack 4 is formed with a plurality of holes for accommodating therein a plurality of sample containers 2. The receptible racks 4 is adapted for collecting at least one sample container 2 from the rack 3.

Bar code is formed at an outer vertical surface of each rack 3 and 4 for identification. Further, bar code is also formed at a bottom of each sample container 2 for identification. The bar code also identifies a content accumulated in the sample container 2.

The automatic storage system 1 includes a storage section 10 and a control section 30 connected thereto. The storage section 10 includes a box-shaped frame 11 formed with a front rectangular opening 11a, a front left door 12 pivotally secured to a vertical left edge of the front rectangular opening 11a, and a front right door 13 pivotally secured to a vertical right edge of the front rectangular opening 11a. A box shaped internal space is provided when these doors 12 and 13 are closed. Casters 18 are connected to a bottom wall of the frame 11 for moving the storage section 10 to a desired site.

Figure 2:
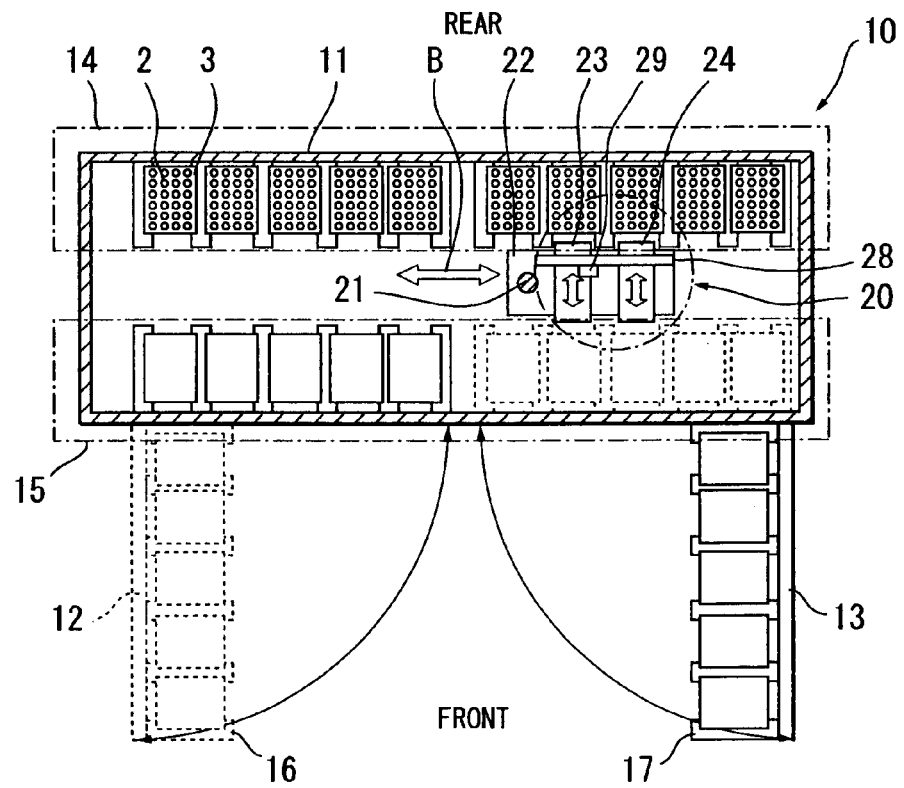
FIG. 2 is a cross-sectional plan view showing the automatic storage system according to the embodiment.

As shown in FIG. 2, first and second shelf sections 14, 15 are installed in the storage section 10 in a juxtaposed fashion for storing therein the plurality of racks 3 and receptible racks 4. The first shelf section 14 is installed at an inner rear vertical wall of the frame 11, and a second shelf section 15 is installed at inner vertical walls of the left and right doors 12, 13. Thus, the second shelf section 15 is divided into left shelf section 16 and a right shelf section 17. As shown in FIGS. 1 and 2, each shelf section 14, 15 has a plurality of shelves extending horizontally and in parallel with each other so as to mount a plurality of racks 3 in their upstanding orientation.

At a space between the first and second shelf sections 14 and 15, a transfer mechanism 20 is provided which is movable in vertical and horizontal directions as shown by arrows A and B in FIGS. 1 and 2. The transfer mechanism 20 includes a vertical rod 21 movable in horizontal direction, a base 22 extending horizontally and movable in vertical direction along the vertical rod 21, and a pair of rack pull-out mechanisms 23, 24 provided on the base 22. The rack pull-out mechanisms 23, 24 are adapted for pulling out a desired rack 3 and a desired receptible rack 4 from the shelf, or returning the pulled out rack 3 and receptible rack 4 to a desired position of a desired shelf. To this effect, the rack pullout mechanisms 23, 24 include slide arms (not shown) movable in frontward/rearward direction as indicated by arrows C and D in FIG. 4 and in a vertical direction, and accessible to a position immediately below a bottom of a desired racks 3 and the receptible rack 4 stored at any one of the shelves in the first and second shelf sections 14,15. The base 22 is provided with a bar code reader 25 for reading the bar code formed on the rack 3 and receptible rack 4.

Figure 3:
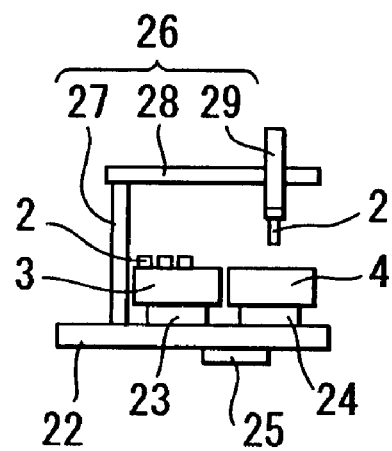
FIG. 3 is a side view showing a transfer section of the automatic storage system according to the embodiment.

As best shown in FIG. 3, a repacking mechanism 26 is provided on the transfer mechanism 20. That is, the repacking mechanism 26 includes a vertical support rod 27 extending from the base 22 and movable in a frontward/rearward direction as shown by an arrow E in FIGS. 4 and 5, a horizontal rod 28 extending from the vertical support rod 27, and a picker mechanism 29 movable along the horizontal rod 28. The picker mechanism 29 is vertically movable and includes a plurality of hand arms for holding a desired one of the sample container 2. The horizontal rod 28 extends over the two rack pull-out mechanisms 23 and 24 so that the picker mechanism 29 can access to the sample containers 2 held on any one of the racks on the two rack pull-out mechanisms 23, 24.

The control section 30 includes a ROM (not shown) storing various operation programs for the transfer mechanism 20 and the repacking mechanism 26. The control section 30 also includes a memory region (not shown) storing data of position of each sample container 2 with respect to the rack 3, data of content of each sample container 2, and data of position of each rack 3 and receptible rack 4. The bar code reader 25 is connected to the control section 30. Further, another bar code reader (not shown) is connected to the control section 30 for reading bar codes of the racks 3, 4 and sample containers 2 as an initial setting. An input device 31 is connected to the control section 30 for inputting various data.

Setting operation for setting the sample containers 2 into the racks 3 and for setting the racks 3 and receptible racks 4 into the shelf sections 14 and 15 will be described. First, data of each sample containers 2 and data of position of each sample container 2 with respect to a rack 3 are read by the bar code reader (not shown), and these data are stored in the memory region of the control section 30. Further, data of each rack 3 and receptible rack 4 are read by the bar code reader (not shown) and these data are also stored in the memory region.

Then, left and right doors 12 and 13 are opened, and the racks 3 and the receptible racks 4 are set at random positions of the shelf sections 14, 15. For example, the racks 3 are set at random position of the shelves on the first shelf section 14, and the receptible racks 4 are set at random position of the shelves on the second shelf sections 15. In this case, because the doors 12 and 13 are opened, access to the first shelf section 14 can be easily made for facilitating setting of the increased numbers of racks 3, 4 onto the first shelf section 14. Moreover, because the second shelf section 15 is provided at the doors 12 and 13, the storage section 10 can provide an increased capacity.

Then, left and right doors 12 and 13 are closed, and the transfer mechanism 20 is operated so as to read by the bar code reader 25 every bar code of the racks 3 and receptible racks 4 set in the shelves. Therefore, data of position of the racks 3 and receptible racks 4 with respect to the shelves are stored in the memory region of the control section 30.

With this process, the racks 3 and receptible racks 4 can be set at any position of the shelves of the first and second shelf sections 14 and 15, and therefore, great numbers of racks 3, 4 can be promptly stored on the shelf sections 14 and 15. Further, positions of all sample containers 2 relative to the racks 3 and positions of the racks 3 and receptible racks 4 can be recognized by the control section 30. In other words, numbers of the receptible racks 4 can be selected at random, because the receptible racks 4 can be stored in both first and second shelf sections 14 and 15. This is advantageous in that increased numbers of vacant receptible racks 4 can be successively pulled out onto one of the rack pull-out mechanisms 23,24 so as to pick up increased numbers of the sample containers 2 to the receptible rack 4.

Figure 4:
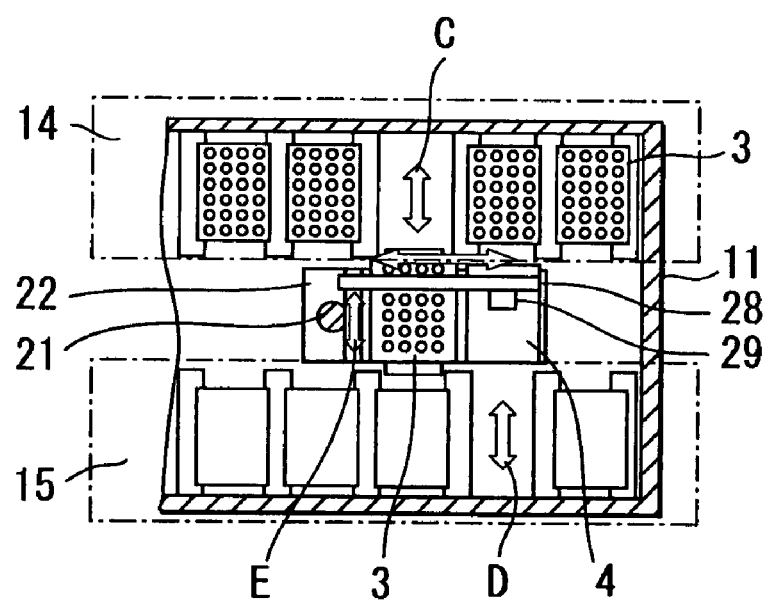
FIG. 4 is a cross-sectional plan view for description of repacking sample containers between a rack stored in a first shelf section and a receptible rack stored in a second shelf section according to the embodiment.
Figure 5:
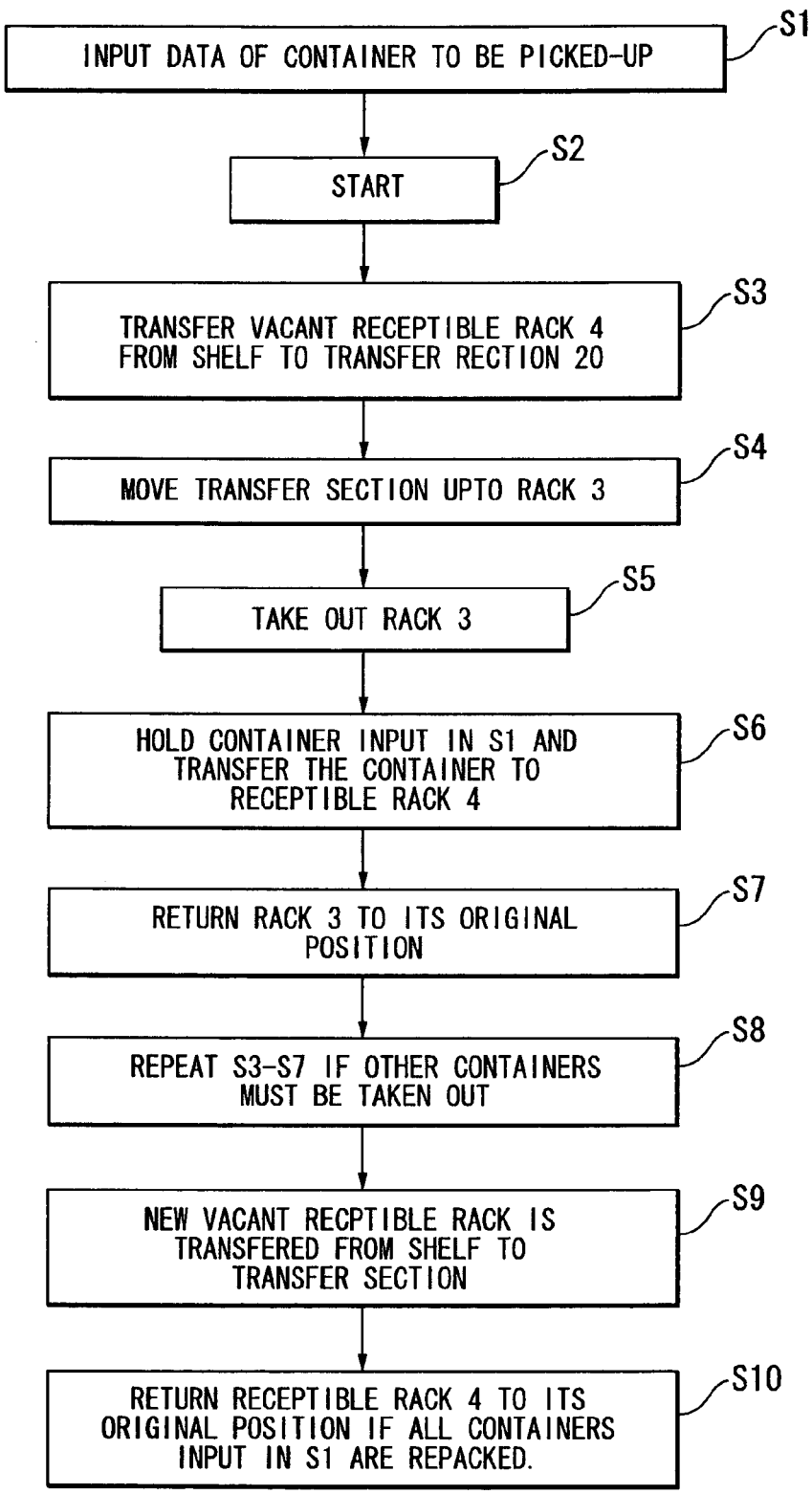
FIG. 5 is a flow chart showing a process of repacking sample containers from the rack(s) to the receptible rack(s) according to the embodiment.

Next, a process for picking up the desired sample container 2 will be described with reference to FIGS. 4 and 5. First, data of the sample container 2 to be picked up is input through the input device 31 connected to the control section 30 (S1), and then the routine is started (S2). The base 22 of the transfer mechanism 20 is moved to a position adjacent to the vacant receptible rack 4, and the receptible rack 4 is pulled out by the rack pull-out mechanism 24, so that the receptible rack 4 is positioned above the base 22 (S3). In the pull-out operation, the slide arm of the rack pull-out mechanism 24 is horizontally moved below the vacant receptible rack 4, and then is moved slightly upwardly, so that the receptible rack 4 is slightly moved away from the shelf. Then, the slide arm is retracted to move the rack 4 above the base 22.

Then, the transfer mechanism 20 is moved so that the other rack pull-out mechanism 23 is brought to a position in confrontation with the specific rack 3 which accommodates the desired sample container 2 input by the input device 31 (S4). Then, the specific rack 3 is transferred onto the rack pullout mechanism 23 (S5). Thus, the specific rack 3 and the vacant receptible rack 4 are positioned side by side as shown in FIG. 4.

Then, the picker mechanism 29 holds the desired sample container 2 in the specific rack 3, and transfers the desired sample container 2 to the receptible rack 4 (S6). Upon completion of the transfer, the specific rack 3 is returned to its original position by the rack pull-out mechanism 23 (S7).

If a plurality of sample containers 2 accommodated in racks different from each other are to be picked up, the above process from S4 to S7 are repeatedly executed. Further, if the first receptible rack 4 is filled with sample containers 2 and a second vacant receptible rack 4 is required for further accommodating therein the remaining desired sample containers 2, the first receptible rack 4 is returned to its original position by the second rack pull-out mechanism 24, and the second pull-out mechanism 24 pulls out the second receptible rack 4 from the shelf, and the routine returns to S4 (S9). When all desired sample containers are repacked into the receptible rack 4, the receptible rack 4 is returned to its original position (S10).

Figure 9:
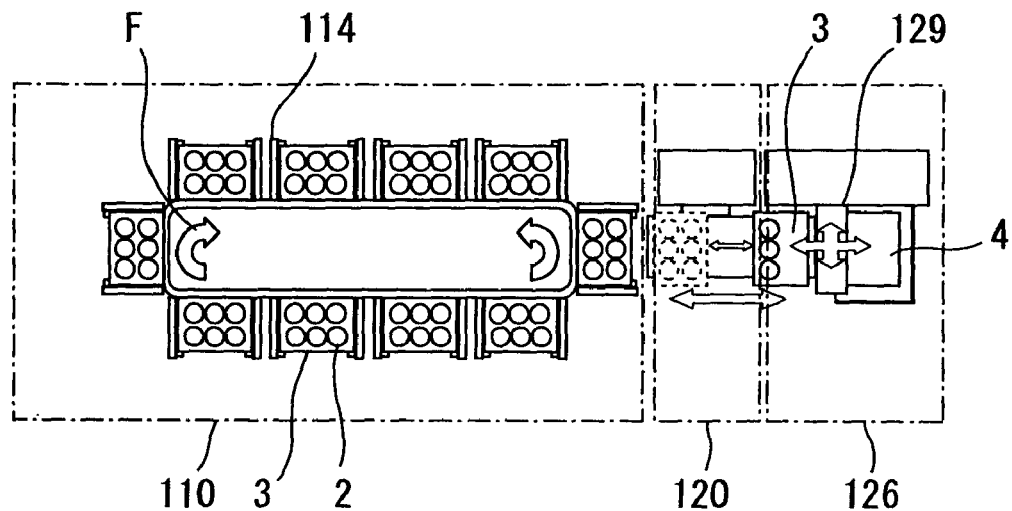
FIG. 9 is a schematic plan view showing a conventional automatic storage system.
Figure 10:
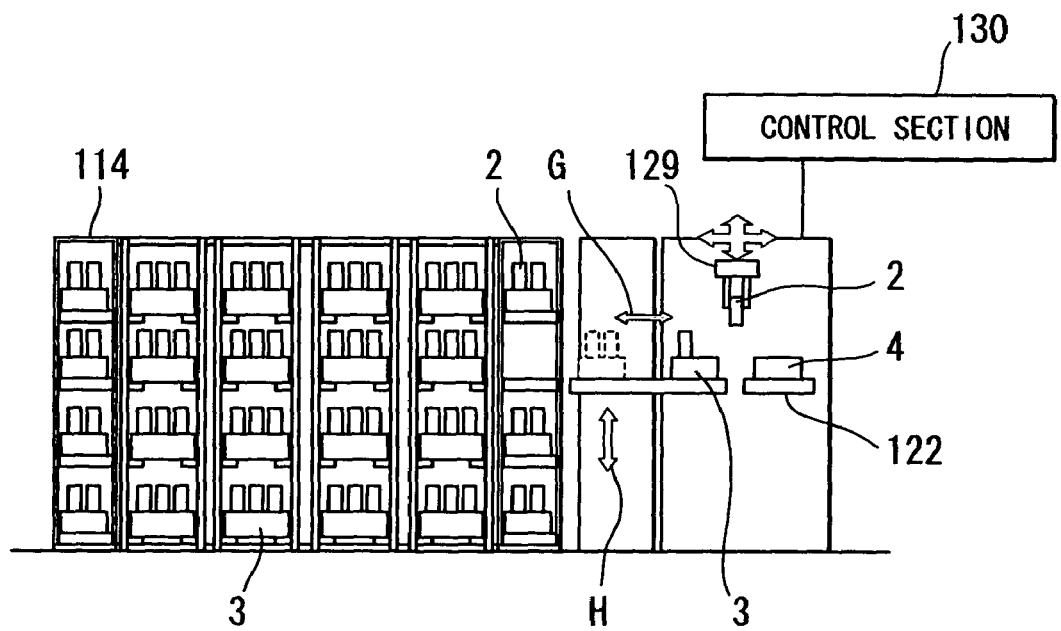
FIG. 10 is a front view showing the conventional automatic storage system.

In the above-described arrangement, since two rack pull-out mechanisms 23 and 24 are provided side by side, repacking of sample containers can be easily performed between two racks 3 and 3 or between the rack 3 and the receptible rack 4. Accordingly, a proper arrangement (positioning) of the sample containers can be provided. Further, since these mechanisms 23, 24 and the picker mechanism 29 of the repacking mechanism 26 are provided on the transfer mechanism 20, it becomes possible to perform repacking operation between two racks 3 and 3 or between the rack 3 and the receptible rack 4 within a space defined between the first and second shelf sections 14 and 15. In other words, it is unnecessary to carry these racks to a different repacking region as seen in the conventional system shown in FIGS. 9 and 10. Consequently, time saving repacking operation can result.

Figure 6:
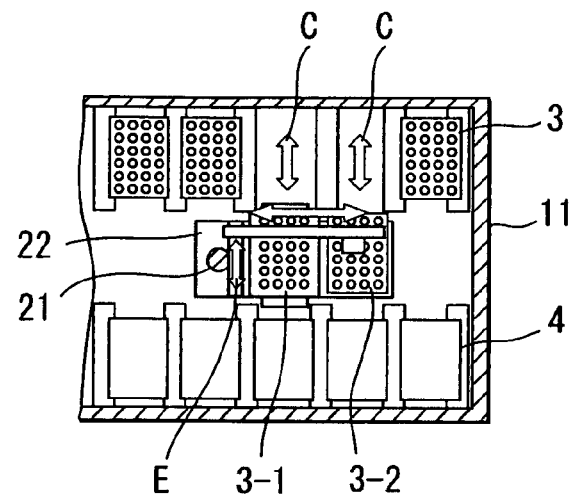
FIG. 6 is a cross-sectional plan view for description of repacking sample containers between two racks stored at the first shelf section according to the embodiment.
Figure 7:
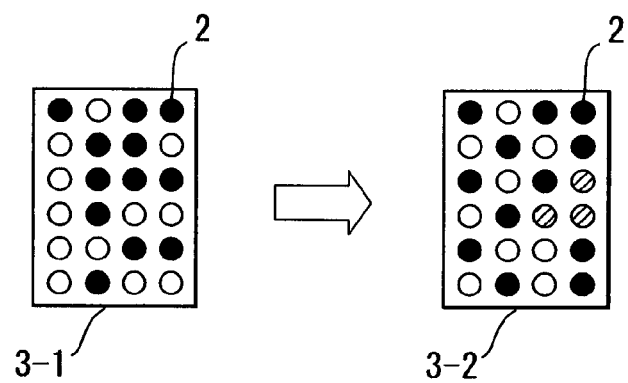
FIG. 7 is a view for description of repacking all sample containers from a rack 3-1 to a rack 3-2 according to the embodiment.

FIGS. 6 and 7 show a process of repacking the sample containers between two racks 3 and 3. In FIG. 7, black circles imply that the sample container are positioned, white circles imply that no sample container is positioned, and hatching circles imply that sample containers have already been positioned. As shown in FIG. 6, two racks 3-1 and 3-2 are respectively pulled out to a position above the base 22 by means of the rack pull-out mechanisms 23 and 24. Then, the picker mechanism 29 moves over the two racks 3-1, and 3-2 so as to shift all sample containers 2 in the rack 3-1 to the desired locations of the rack 3-2 as shown in FIG. 7.

Upon completion of repacking, each rack is returned to each original position. Alternatively, a newly vacant rack 3-1 can be used as a receptible rack 4. Further alternatively, a rack collecting section (not shown) can be provided for collecting the newly vacant rack 3-1.

Figure 8:
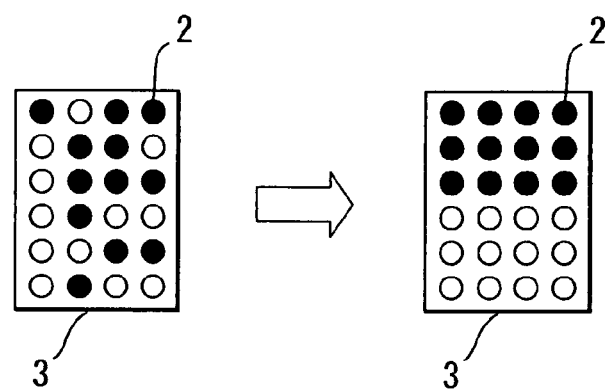
FIG. 8 is a view for description of relocating all sample containers in good order in an identical rack according to the embodiment.

FIG. 8 shows relocations of the sample containers 2 in the identical rack 3 for proper arrangement of the containers 2. Prior to the relocations, the sample containers 2 are located in a scattered manner in the rack 3. By operating the rack pull-out mechanism 23 or 24 and by operating the picker mechanism 29, the sample containers 2 can be relocated in a tight fashion. Consequently, space in the storage section 10 can be effectively utilized.

In the present embodiment, sample containers 2 can be automatically stored into the storage section 10. First, the bar codes of the sample containers 2 are read by the bar code reader (not shown), and the sample containers 2 to be stored are set in the receptible rack 4. Then, storage of the sample containers 2 is input into the control section 30 through the input device 31. Then, the rack pull-out mechanism 24 (or 23) pulls out the receptible rack 4 to a position above the base 22. Because the control section 30 recognizes the setting manner of the sample containers of the various racks 3, the control section 30 selects a suitable rack 3 capable of setting additional sample containers 2 and already stored in one of the first and second shelf sections 14 and 15. The selected rack 3 is then pulled out by the remaining rack pull-out mechanism 23 (or 24), and the sample containers 2 are transferred from the receptible rack 4 to the selected rack 3 by the picker mechanism 29. Thus, the sample containers can be automatically stored in the proper rack.

While the invention has been described in detail with reference to specific embodiments thereof, it would be apparent to those skilled in the art that various changes and modifications may be made therein without departing from the spirit and scope of the invention. For example, a temperature control device can be installed in the box-shaped frame 11 if the testing samples in the containers 2 require temperature control.

Further, the frame 11 and doors 12, 13 can be formed of punched metal plate where a plurality of perforations are penetratingly formed throughout the thickness so as to provide free ventilation between inner and outer space of the storage section 10. Thus, temperature control with respect to sample containers 2 stored in the storage section 10 can be performed through the perforations even if the storage section 10 is not provided with temperature control device, as long as the storage section 10 is installed in a room equipped with an air conditioning system. Accordingly, extra space for installing the temperature control device is not required in the storage section 10, to thus increase installation space for the sample containers 2.

Further, in the above-described embodiment, the slide arm of each rack pull-out mechanisms 23, 24 is movable in vertical direction as well as frontward/rearward direction for an access to the position immediately below the bottom of the desired racks 3 and the receptible rack 4 stored at the shelf. However, vertical movement of the slide arm can be eliminated by providing a retractable pawl on the upper surface of the slide arm. The retractable pawl retracts when the pawl is moved past the bottom surface of the rack, and projects when the pawl has finished passing so as to engage a rear vertical wall of the rack. Further, in the above-described embodiment, bar code is formed in each receptible rack 4 for recognition of positions and numbers of the receptible racks 4. However, instead of formation of the bar codes, positions and numbers of the receptible racks 4 can be input through the input device 31 into the control section 30.

What is claimed is:

1. An automatic storage system for storing sample containers held in racks, comprising:
    an outer frame having a rear wall, a front side formed with a front opening, and a front door pivotally movably secured to the front side for opening and closing the front opening;
    a first shelf section positioned in the outer frame and supported by the rear wall for storing a plurality of racks in which a plurality of sample containers are installable;
    a second shelf section positioned in the outer frame and secured to the front door for storing a plurality of racks in which a plurality of sample containers are installable, the second shelf section being pivotally movable to take a first position and a second position, the second shelf section being disposed side by side with the first shelf section having a space therebetween when the second shelf section takes the first position, and the second shelf section being disposed substantially perpendicular to the first shelf section when the second shelf section takes the second position, the sample containers held in the racks being stored in the first and the second shelf sections when the second shelf is in the second position;
    a transfer section movable in the space and comprising a rack pull-out mechanism for pulling out the rack from either one of the first and second shelf sections, maintaining the pulled-out rack on the rack pull-out mechanism and returning the pulled-out rack to one of the first and second shelf sections, the pulling out and returning the rack being performed when the second shelf section is at the first position, wherein the transfer section comprises a horizontally moving member movable along the space and a base connected to the horizontally moving member and vertically movable along the horizontally moving member, the rack pull-out mechanism being disposed on the base; and
    a control section connected to the transfer section managing operations thereof and managing position data of the racks and sample containers.

2. The automatic storage system as claimed in claim 1, further comprising a repacking mechanism provided on the transfer section for moving at least one sample container from a first position on the rack to a second position on the identical or different rack held on the rack pull-out mechanism, the control section being also connected to the repacking mechanism for managing operation thereof.

3. The automatic storage system as claimed in claim 2, wherein the rack pull-out mechanism comprises:
    a left pull-out mechanism disposed on the base and accessible to a first rack stored in one of the first and second shelf sections; and
    a right pull-out mechanism disposed on the base and beside the left pull-out mechanism in the lengthwise direction of the space, the right pull-out mechanism being accessible to a second rack stored in one of the first and second shelf sections, whereby two racks are positioned side by side while being held on the left pull-out mechanism and the right pull-out mechanism, respectively.

4. The automatic storage system as claimed in claim 3, wherein the repacking mechanism comprises:
    a support rod positioned on the base and movable in a frontward/rearward direction of the frame, the support rod extending in the lengthwise direction of the space over the left pull-out mechanism and the right pull-out mechanism; and a picker mechanism supported on the support rod and movable therealong, the picker mechanism being also movable in the vertical direction and having an arm for holding the sample container supported by the rack on one of the left and right pull-out mechanisms.

5. The automatic storage system as claimed in claim 1, wherein the front door comprises a left front door, and a right front door, the second shelf section being divided into left shelf section secured to the left front door and a right shelf section secured to the right front door.

6. The automatic storage system of claim 1 further comprising: a vertical rod with one end attached to the transfer section supporting a repacking mechanism.

7. The automatic storage system as claimed in claim 1, wherein each rack is formed with a bar code for identification, the automatic storage system further comprising:

a bar code reader disposed at the transfer section and connected to the control section for reading each bar code and transmitting data of position of each rack on the first and second shelf sections.

8. The automatic storage system as claimed in claim 7, wherein the plurality of racks comprise:

a first plurality of racks for setting therein the sample containers for storage in the first and second shelf sections; and a second plurality of racks serving as receptacle racks for collecting therein the sample containers from the first plurality of racks, the second plurality of racks being also storable in the first and second shelf sections.

9. The automatic storage system as claimed in claim 1, further comprising a temperature control device disposed in the outer frame.

10. The automatic storage system as claimed in claim 1, wherein the outer frame is formed with a plurality of venting perforations.

11. The automatic storage system as claimed in claim 1, further comprising casters provided at a bottom of the outer frame.

12. An automatic storage system for storing sample containers as defined in claim 1, wherein the second shelf section is divided into a first portion and a second portion, the first portion being secured to move pivotally in one direction and the second portion being secured to move pivotally in an opposite direction.

13. An automatic storage system for storing sample containers, comprising:

a plurality of racks each adapted to hold a plurality of sample containers, the racks including at least a first rack which holds a sample container to be stored and a second rack which has a vacant position to receive a sample container;

a first shelf section for storing the racks, extending in at least one direction;

a second shelf section placed extending along the first shelf section with a space therebetween and being movable to take a first position and a second position, the racks including the first rack and the second rack being stored in at least one of the first and the second shelf section when the second shelf section is at the second position;

a transfer mechanism movable in the space between the first and the second shelf sections and having a first handling means and a second handling means, the transfer mechanism pulling out the first and the second racks by using the first handling means from at least one of the first and the second shelf section and transferring the sample container from the first rack to the second rack by using the second handling means when the second shelf section is at the second position, wherein the first handling means and second handling means are disposed on a common vertically movable base with the second handling means supported by a rod having one end connected to the common vertically movable base; and a control section connected to the transfer mechanism managing operations thereof and managing position data of the racks and the sample containers.

14. An automatic storage system for storing sample containers as defined in claim 13, wherein the second shelf section is movable to take the first position at which the second shelf section is disposed in parallel with the first shelf section and the second position at which the second shelf section is disposed substantially perpendicular to the first shelf section.

15. An automatic storage system for storing sample containers as defined in claim 13, wherein the first handling means of the transfer mechanism comprises a first rack handling means to place the first rack on a base and a second rack handling means to place the second rack on the base.

16. An automatic storage system for storing sample containers, comprising:

a plurality of racks each adapted to hold a plurality of sample containers, the racks including at least a first rack which holds a sample container to be stored and a second rack which has a vacant position to receive a sample container;

a first shelf section for storing the racks, extending in at least one direction;

a second shelf section placed extending along the first shelf section with a space therebetween and being movable to take a first position and a second position, the racks including the first rack and the second rack being stored in at least one of the first and the second shelf section when the second shelf section is at the second position;

a transfer mechanism movable in the space between the first and the second shelf sections and having a pull-out mechanism and a repacking mechanism, the transfer mechanism pulling out the first and the second racks by using the pull-out mechanism from at least one of the first and the second shelf section and transferring the sample container from the first rack to the second rack by using the repacking mechanism, wherein the pull-out mechanism and the repacking mechanism are disposed on a common vertically movable base with the repacking mechanism supported by a rod having one end connected to the common vertically movable base; and a control section connected to the transfer mechanism managing operations thereof and managing position data of the racks and the sample containers.

* * * * *